United States Patent [19]

Venkatasetty

[11] Patent Number: 4,948,490
[45] Date of Patent: Aug. 14, 1990

[54] TETRAALKYLAMMONIUM ION SOLID ELECTROLYTES

[75] Inventor: H. V. Venkatasetty, Burnsville, Minn.

[73] Assignee: Honeywell Inc., Minneapolis, Minn.

[21] Appl. No.: 388,307

[22] Filed: Jul. 28, 1989

Related U.S. Application Data

[63] Continuation of Ser. No. 161,269, Feb. 19, 1988, abandoned, which is a continuation-in-part of Ser. No. 21,957, Mar. 5, 1987, abandoned.

[51] Int. Cl.$^5$ .............................................. G01N 27/30
[52] U.S. Cl. .................................... 204/412; 204/415; 204/421; 204/431; 429/192; 429/194; 429/198; 429/201; 427/77; 427/240
[58] Field of Search ............... 204/412, 421, 431, 415; 429/190, 192, 194, 198, 199, 201; 427/77, 240

[56] References Cited

U.S. PATENT DOCUMENTS

| | | | |
|---|---|---|---|
| 1,484,937 | 1/1980 | Tataria et al. | 204/1 T |
| 4,347,302 | 8/1982 | Gotman | 427/240 |
| 4,406,770 | 9/1983 | Chan et al. | 204/412 |
| 4,521,290 | 6/1985 | Venkatasetty | 204/412 |
| 4,522,690 | 6/1985 | Venkatasetty | 204/412 |
| 4,537,843 | 8/1985 | Shishikura et al. | 429/198 |
| 4,670,127 | 6/1987 | Ritter et al. | 204/418 |

FOREIGN PATENT DOCUMENTS 3311313 10/1984 Fed. Rep. of Germany ...... 429/198

OTHER PUBLICATIONS

Solid Ionic—These Unusual Materials Applications in High-Energy-Density. C&EN, May 20, 1985, pp. 42–44:50–53.
Poly-Ethers as Solid Electrolytes, Armand et al, pp. 131–136.
Polyphosphazene Solid Electrolytes, J. Am. Chem. Soc. 1984, Blonsky et al, pp. 6854–6855.
D. F. Shriver and G. C. Farrington, Solid Ionic Conductors, May 20, 1985, C&EN pp. 42–57.
I. Kelly, J. R. Owen, and B. C. H. Steele, Mixed Polyether Lithium-Ion, J. Electroanal Chem., 168 (1984) 467–478.

Primary Examiner—John F. Niebling
Assistant Examiner—Kathryn Gorgos
Attorney, Agent, or Firm—Gregory A. Bruns

[57] ABSTRACT

Electrochemically stable, non-hygroscopic ionically conducting solid electrolyte films for use in environmental sensors feature an amount of tetraalkylammonium salt in one or more aprotic solvents together with an amount of organic polymeric matrix material and an amount of a plasticizer, if desired.

26 Claims, 3 Drawing Sheets

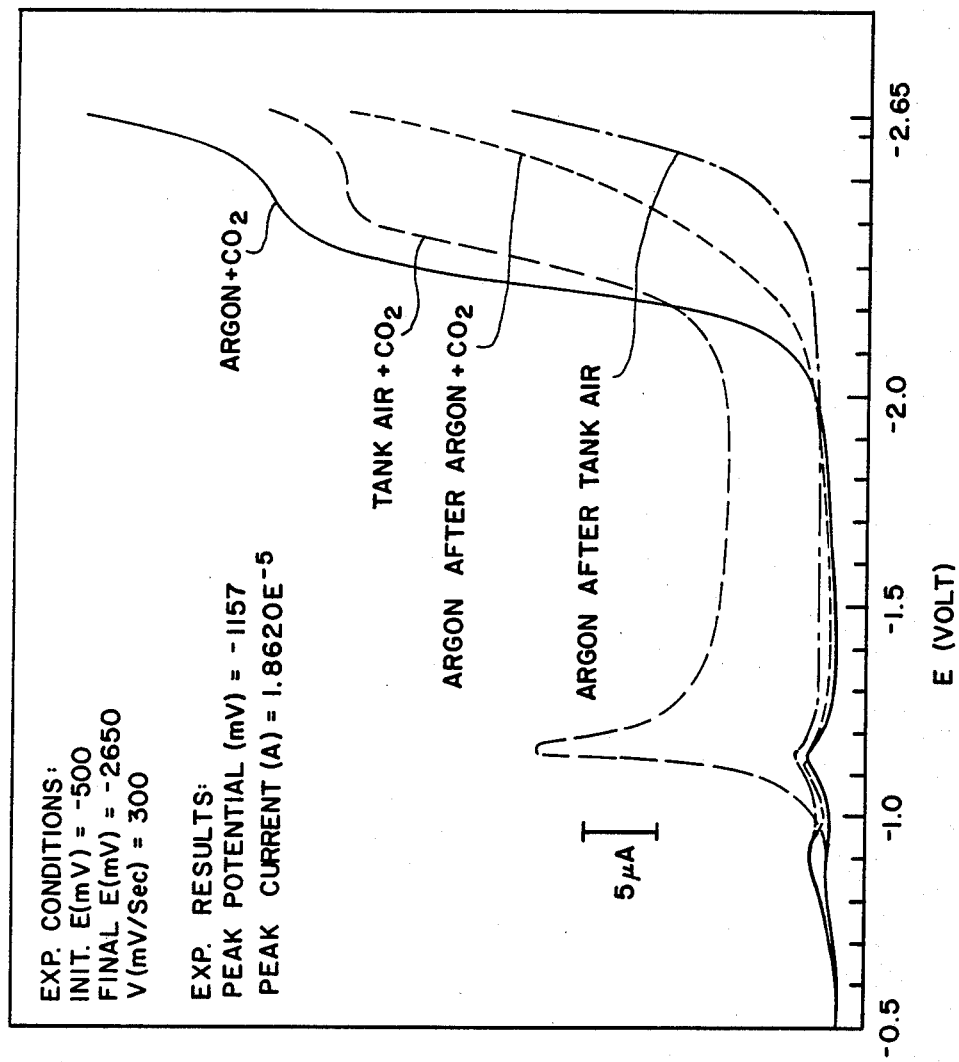
Fig. 2 MULTI-GAS SENSOR CELL RESPONSE TO TANK AIR AND CARBON DIOXIDE AND ARGON AND CARBON DIOXIDE

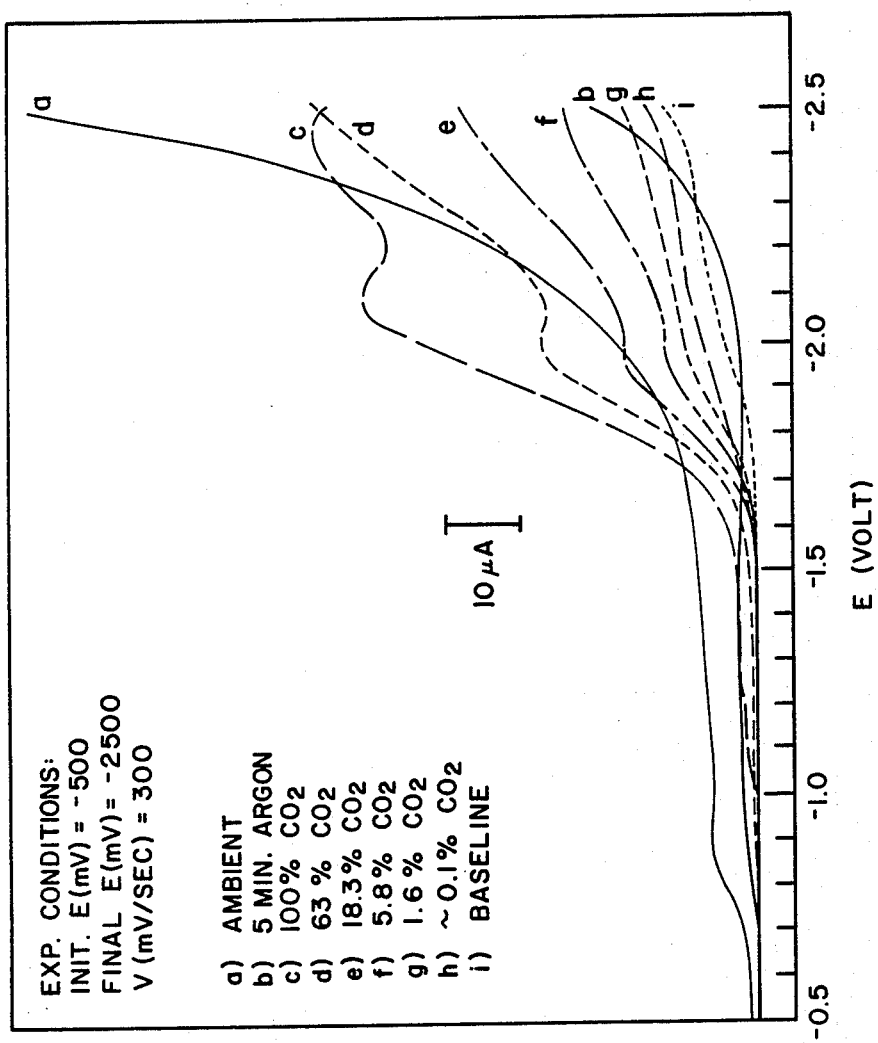
Fig. 3    MULTI-GAS SENSOR CELL RESPONSE TO VARYING CONCENTRATIONS OF CARBON DIOXIDE

TETRAALKYLAMMONIUM ION SOLID ELECTROLYTES

No. 07/161,269 filed Feb. 19, 1988, now abandoned, which is a continuation-in-part of Ser. No. 21,957 Mar. 5, 1987, abandoned.

BACKGROUND OF THE INVENTION

1. Field of the Invention

The present invention relates generally to electrochemical measurement of the concentration of one or more species of interest in a mixture of gases and, more particularly, environmentally stable polymeric based solid electrolyte films for use in gas sensors.

2. Description of the Prior Art

Electrochemical reactions based on oxidation and reduction of metals and compounds at an electrode are highly selective because of the characteristic redox potential at which oxidation or reduction of the electroactive species occurs. Selection of the electrode material in combination with an electrolyte solution system has become very important in determining sensitivity and selectivity. This is especially important in situations where one species is sought to be determined quantitatively in the presence of other species which may exhibit similar reactions.

Electrochemical gas sensors utilizing aqueous acidic or basic electrolyte solutions are well known. Those sensors, however, have significant limitations. They have a limited operating life, i.e., generally six months or less. They are relatively expensive because they are not amenable to batch fabrication techniques due to the use of liquid electrolytes. In addition the liquid electrolyte is not environmentally stable and is also subject to evaporation.

Sensors using non-aqueous electrolytes have also been used in the prior art, for example, to sense the presence of carbon monoxide (CO) and other toxic gases such as nitrogen oxides ($NO_x$) in the environment. One such system is shown in U.S. Pat. No. 4,522,690 to H. V. Venkatasetty, the inventor in the present application. That system included a non-aqueous, aprotic electrolyte system of approximately 1.0 M $LiClO_4$ in $\gamma$-butyrolactone or approximately 0.75 M $LiClO_4$ in propylene carbonate gelled with a small amount of polyethylene oxide (about 10% by weight based on the other constituents).

Gelled, ion conducting polymer electrolytes have also been demonstrated in lithium secondary or rechargeable batteries. These materials are highly reactive and require non-aqueous environments.

It is noteworthy that these prior art gelled or solid electrolyte films have all contained or depended on alkali metal ion or alkali metal, usually lithium containing compounds to produce successful embodiments. However, alkali metal ion conducting electroylte films are quite reactive and highly hygroscopic and must be used in hermetically sealed cells. Such electrolyte materials cannot be used in exposed environmental sensors; therefore, nonhygroscopic components which are electrochemically stable to ambient conditions are required for any kind of environmental sensor.

Thus, a definite need has existed in the art for an environmentally stable, relatively solid electrolyte which can be utilized in electrochemical gas sensing. There is also a need for such a gas sensor which is relatively low cost such as one which could be produced by large batch fabrication techniques.

SUMMARY OF THE INVENTION

By means of the present invention, successful ionically conducting solid electrolyte films which are environmentally stable and which exhibit sufficient conductivity to be quite useful in 9as detectors have been realized. Thin films (about 1–5 mil) of these electrolytes have room temperature conductivities in the usable range of $10^{-5}$–$10^{-6}$ ohm$^{-1}$ CM$^{-1}$. Cells made using these solid electrolyte films show excellent gas sensing properties and can readily be adapted to high volume batch processing.

The ionically conducting polymeric solid electrolyte films of the invention are prepared as in examples below, from an amount of tetraalkylammonium salt in one or more aprotic solvents together with an amount of a suitable complexing polymer which forms a solid matrix. An amount of plasticizer may also be added. Preferred aprotic solvents include acetonitrile, $\gamma$-butyrolactone, dimethylformamide (DMF), propylene carbonate, tetrahydrofuran (THF), and other similar materials. The preferred plasticizer or plasticizing agent is polyethylene glycol dimethyl ether (PEGDME). The preferred tetraalkylammonium salts include tetraethylammonium hexafluorophosphate ($Et_4NPF_6$) and tetrabutylammonium hexafluorophosphate ($Bu_4NPF_6$). The preferred polymeric complexing matrix material is polyethylene oxide (PEO). Other polymers such as polypropylene oxide (PPO), polyvinylidene fluoride (PVDF) and polyacrylonitrile (PACN) are examples of materials which may also be used.

The solid electrolytes of the invention are, by definition, solid materials usually in thin pliable film form that allow ions to move through them when a potential is applied between electrodes on which the films are deposited. The ionically conducting, polymer-based thin film materials of the invention have tetraalkylammonium based salts or electrolytes incorporated into an organic polymer matrix by processing with a solvent or solvent and plasticizer mixture at an elevated temperature. The mixture may be spin coated as on the electrode structure of a sensor, for example, which is normally on a dielectric substrate or any other desired substrate. The solvent or solvent plasticizer mixture is removed from the thin films by drying them in a vacuum at elevated, e.g. 30°–150° C., temperature, if indicated. If an amount of plasticizer is employed, it is normally incorporated in the mixture and later removed with the solvent by the vacuum drying.

The use of the plasticizer together with the heating of the mixture seems to enhance ionic conductivity. It is believed to transform the tetraalkylammonium salts and the material of the organic polymer matrix from forms or structures which are basically crystalline in nature to forms which are to a greater or lesser degree amorphous or platicized amorphous states. While, the precise mechanism or exact final form are not presently known, it appears that higher temperatures accomplish higher amorphous fractions.

The ionically conducting electrolyte films of the invention exhibit excellent environmental stability, are readily fabricated by batch processing and electrochemical cells using such gelled electrolyte films exhibit very good environmental gas sensing.

BRIEF DESCRIPTION OF THE DRAWINGS

FIGS. 2 and 3 are plots of responses of a cell made in accordance with the invention to certain gases and gaseous mixtures.

DESCRIPTION OF THE PREFERRED EMBODIMENTS

Figure 1:
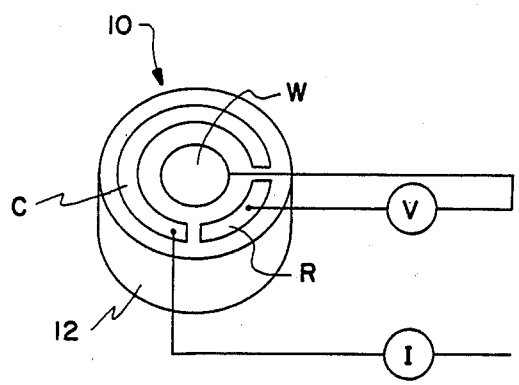
FIG. 1 depicts a typical sensing cell for use with the solid electrolyte film of the present invention.

One of the many possible embodiments of a single cell sensor utilizing the film of the present invention is illustrated in simplified form in FIG. 1. The cell shown generally at 10 has an electrode carrying substrate member which may be a dielectric substrate such as silicon dioxide ($SiO_2$) such as that illustrated at 12 and carries a single set of three electrodes including a working or sensing electrode, a reference electrode and a counter electrode as indicated by W, R and C, respectively. In order for the IR drop to be minimized, the electrodes should be coplaner and very small, however, any conventional pattern such as an interdigital electrode pattern may be used.

Figure 1A:
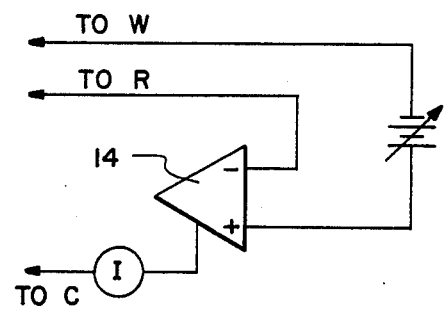
FIG. 1A is a schematic diagram of a typical circuit for use with the cell of FIG. 1.

An adjustable potential source is connected across the sensing or working electrodes and the reference electrode and the current is measured between the working and counter electrodes. A voltage exists but no current flows from the reference electrode to the sensing electrode. Preferred form of this energizing circuit may include an operational amplifier 14 as shown in FIG. 1A wherein no current flows in the feedback loop from the reference electrode to the negative input of the operational amplifier 14. The variable source of external potential may take any desired form in which the potential of the working electrode is varied with respect to the reference electrode in order to achieve reduction or oxidation of various species sought to be determined by the electrochemical cell.

Thin Film Electrolyte Preparation EXAMPLES 1–15

Solutions of polyethylene oxide (PEO mol. wt. ~100,000) and tetraalkylammonium salts including, in examples 1–7, tetraethylammonium hexafluorophosphate ($Et_4NPF_6$) and, in examples 8–15, tetrabutylammonium hexafluorophosphate ($Bu_4NPF_6$) in the molar ratio of about 9:1 and 12:1 (PEO/salt) were made in propylene carbonate with known amounts of polyethylene glycol dimethyl ether (PEGDME) as a plasticizer. The solution was stirred with a magentic stirrer on a hotplate (about 60 degrees C.) until a homogenous paste was obtained. Using a spin coater, films of different thickness were coated on a dielectric substrate ($SiO_2$) or on a substrate containing the electrode pattern for an electrochemical sensor. These films were dried at about 70 degrees C. in a vacuum oven, cooled, then removed by peeling off from the silicon dioxide substrate. Of course any suitable combination of temperature and vacuum may be employed to accomplish the desired solvent and/or plasticizer evaporation. Variations would occur to those skilled in the art. While higher molecular weight polymers can be used, the lower molecular weight (approximately 100,000) PEO has exhibited better qualities with respect to dissolving in solvents. It will be appreciated that the electrolyte film thickness is related to relative ingredient proportions, including MW of polymer, temperature, spin speed and spin time, etc. and can be controlled as desired.

The polymeric complexing material, of course, is one which not only provides the desired gelled or film matrix but also is one which provides proper complexing with the cation of the electrolyte salt. The complexing must at the same time allow rapid ion migration within the matrix to achieve the necessary conductance. The oxygen atoms of PEO ($CH_2-CH_2-O-$)$_n$ and the nitrogen in polyacrylonitrile

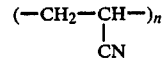

for example, complex with the tetraalkylammonium cations of the salt, such as the $(C_2H_5)_4 N^+$ of tetraethylammonium hexafluorophosphate (($C_2H_5)_4NPF_6$) and the $(C_2H_5)_4 N^+$ of tetrabutylammonium hexafluorophosphate (($C_4H_{10})_4NPF_6$). The relatively large size of the tetraalkylammonium cations involved results in a correspondingly low charge density and, thus, the complexing is relatively weak. This allows easy, and relatively rapid ion migration within the matrix thereby enhancing conductivity.

As additional information, it should be kept in mind, of course, that ionic conductivity in solid electrolyte materials, unlike electronic conductivity or electron migration, is achieved by the process of diffusion in which the cations migrate from one oxygen atom to another assisted by the motion of the polymer. This phenomenon is illustrated and described in greater detail by D. F. Shriver and G. C. Farrington in the May 20, 1985 issue of C&E News at pp 42–57.

It is also important to note that the aprotic organic solvent, such as propylene carbonate, that is used to mix or blend the complexing matrix polymer and the electrolyte salt for processing into the solid electrolyte system is thereafter removed from the mixture by gentle or moderate heating under vacuum. The plasticizer, such as polyethylene glycol dimethyl ether, is normally added to the mixture to increase ionic conductivity by converting some or substantially all of the structure from crystalline to an amorphous form or a plasticized amorphous form in the solid film. Ionic conductivity has been found generally to increase with the increase in degree that the electrolyte salt is converted to the amorphous state. This appears to increase with the amount of plasticizer used and the evaporation temperature. The polyethylene glycol dimethyl ether or other plasticizer added during film preparation is also removed from the films with the solvent by the vacuum heating. Mixtures, molar ratios, and the like preferred to in this specification which include solvent and or plasticizers refer to the compositions prior to any drying step.

The interrelationships between the polymeric complexing matrix material, plasticizer, if used, electrolyte salt and aprotic solvent allow many variations in electrolyte physical properties and conductivity. These, for example, can be based on variations in composition, in the molar ratio between polymer and electrolyte salt, amount of plasticizer, etc., to achieve desired properties in the final film depending on the application involved.

While particular illustrative examples have demonstrated the use of ethyl and butyl tetraalkylammonium phosphates in the electrolyte, tetramethylammonium phosphate ($Me_4NPF_6$) and tetrapropylammonium phosphate ($Pr_4NPF_6$) have also been used and it is contemplated that other alkyls will work. Still other compounds would occur to those skilled in the art which would fit the described parameters.

In the Examples, molar ratios of 9:1 and 12:1 (PEO to salt) are illustrated. It is contemplated that ratios from about 5:1 to 15:1 will work successfully, however. Of course, the ratios involving other polymer complexing materials will also vary. In addition, while about 20% by weight of PEGDME plasticizer as used in the examples is the preferred amount, other electrolytes demonstrated a usable range of from about 5% to 30% by weight of PEGDME.

The conductivities of the prepared example films were measured using nonreversible metal electrodes (Pt or SS) pressed against the film and measuring A.C. impedance of the electrolyte film under dry nitrogen atmosphere. A Hewlett-Packard Impedance Analyzer #4192A operating over the frequency range 5 Hz to 13 MHz was used. The results for electrolytes using $Et_4NPF_6$ (examples 1-7) and $Bu_4NPF_6$ (examples 8-15) are conveniently summarized in Table I, below.

TABLE 1
Properties of Ionically Conducting Electrolyte Films

| Salt (Molarity) | PEO: Salt Molar Ratio | PEGDME Wt. % | Film Thick. (mil) | Cond. @ 25° C. $ohm^{-1} cm^{-1}$ | Avg. Cond. $(ohm^{-1} cm^{-1})$ |
|---|---|---|---|---|---|
| $Et_4NPF_6$ (Examples 1-7) | | | | | |
| 0.3 | 9:1 | 20.14 | 6.9 | $7.8 \times 10^{-6}$ | |
| 0.2 | 9:1 | 20.14 | 1.5 | $4.5 \times 10^{-6}$ | $6.5 \times 10^{-6}$ |
| 0.3 | 9:1 | 20.14 | 6.2 | $7.1 \times 10^{-6}$ | |
| 0.3 | 12:1 | 20.13 | 0.8 | $7.0 \times 10^{-6}$ | |
| 0.3 | 12:1 | 20.13 | 0.8 | $7.0 \times 10^{-6}$ | $9.5 \times 10^{-6}$ |
| 0.3 | 12:1 | 20.13 | 3.1 | $9.1 \times 10^{-6}$ | |
| 0.3 | 12:1 | 20.13 | 1.9 | $1.5 \times 10^{-6}$ | |
| $Bu_4NPF_6$ (Examples 8-15) | | | | | |
| 0.3 | 9:1 | 20.13 | 3.0 | $1.0 \times 10^{-5}$ | |
| 0.3 | 9:1 | 20.13 | 1.5 | $3.1 \times 10^{-6}$ | $5.8 \times 10^{-6}$ |
| 0.3 | 9:1 | 20.13 | 2.1 | $7.9 \times 10^{-6}$ | |
| 0.3 | 9:1 | 20.13 | 7.1 | $2.2 \times 10^{-6}$ | |
| 0.3 | 12:1 | 20.20 | 1.3 | $1.1 \times 10^{-6}$ | |
| 0.3 | 12:1 | 20.20 | 5.6 | $8.4 \times 10^{-6}$ | $1.44 \times 10^{-5}$ |
| 0.3 | 12:1 | 20.20 | 2.4 | $2.9 \times 19^{-5}$ | |
| 0.3 | 12:1 | 20.20 | 6.6 | $9.2 \times 10^{-6}$ | |

Thin films of these electrolytes were deposited on a gold electrode pattern for an electrochemical sensor cell such as that of FIG. 1. The substrate material was silicon dioxide. The electrochemical cell was attached to a fixture with contact wires soldered onto the electrodes and packaged for letting a known concentration of carbon dioxide in air and/or argon into the sensor cell.

The sensor cell was interrogated by a voltammetric technique and scanned linearly in the cathodic range from −0.50 to 2.3 V vs. Pt pseudo reference electrode. With argon gas over the cell and voltage scanning, a small peak was found around 1.15 V due to residual oxygen in the cell (FIG. 2). In the presence of tank air, the oxygen peak amplitude increased at about 1.15 V and in the presence of carbon dioxide in air (10%), in addition to the oxygen peak, there is a new peak around 2.3 V due to the electrochemical reduction of carbon dioxide (FIG. 2). Similar experiments conducted with about 0.1% of carbon dioxide in air show carbon dioxide peak around −2.1 V (FIG. 3). The current concentration relationship for different concentrations of carbon dioxide in air using a thin film electrolyte in an electrochemical cell is shown in FIG. 3. Nonlinearity in current concentration relation at the low end of the carbon dioxide concentration can be attributed to the fact that the cell packaging had not been optimized for low concentration measurement and to the long path length required for the gas to reach the electrode surface.

Thus, in accordance with the invention, ionically conducting thin film solid polymer complexed electrolytes containing tetraalkylammonium cations have been found to be quite stable in ambient surroundings. Room temperature conductivities of these films are in the range $10^{-6}$ to $10^{-5} ohm^{-1} cm^{-1}$. Preliminary studies of these films in electrochemical gas sensors show that carbon dioxide gas in air and/or argon can be detected easily to the level of about 0.1% (1000 ppm). Optimization of film properties should allow one to detect 100ppm or even less of carbon dioxide in air. Results are reproducible and they appear to be very promising for long life and low cost electrochemical gas sensors.

I claim:

1. An environmentally stable, solid, ionically conductive electrolyte system consisting essentially of a composite of an amount of plasticizer material, an amount of symmetrical tetraalkylammonium electrolyte salt and an amount of organic, polymeric complexing matrix material containing donor atoms capable of complexing with the cations of the electrolyte salt wherein the composite is predominately in an amorphous form.

2. The electrolyte of claim 1 wherein said salt is selected from the group consisting of $(CH_3)_4NPF_6$, $(C_2H_5)_4NPF_6$, $(C_3H_7)_4NPF_6$, $(C_4H_9)_4NPF_6$, and mixtures thereof.

3. The electrolyte of claim 2 wherein said polymeric matrix material is selected from the group consisting of polyethylene oxide, polyproplyene oxide, polyvinylidene fluoride and polyacrylonitrile.

4. The electrolyte of claim 3 wherein said plasticizer is polyethylene glycol dimethyl ether.

5. The electrolyte of claim 2 wherein said plasticizer is polyethylene glycol dimethyl ether.

6. A solid, environmentally stable, ionically conductive electrolyte system in the form of a self-supporting pliable film consisting essentially of a composite of an amount of plasticizer material, an amount of symmetrical tetraalkylammonium electrolyte salt and an amount of organic polymeric complexing matrix material containing donor atoms capable of complexing with the cation of the electrolyte salt, wherein the composite film material is substantially in an amorphous state.

7. The electrolyte of claim 6 wherein said salt is selected from the group consisting of $(CH_3)_4NPF_6$, $(C_2H_5)_4NPF_6$, $(C_3H_7)_4NPF_6$, $(C_4H_9)_4NPF_6$, and mixtures thereof.

8. The electrolyte of claim 7 wherein said polymeric matrix material is selected from the group consisting of polyethylene oxide, polyproplyene oxide, polyvinylidene fluoride and polyacrylonitrile.

9. The electrolyte of claim 8 wherein said plasticizer is polyethylene glycol dimethyl ether.

10. The electrolyte of claim 7 wherein said plasticizer is polyethylene glycol dimethyl ether.

11. The electrolyte of claim 6 wherein said salt is selected from the group consisting of $(C_2H_5)_4NPF_6$, and $(C_4H_9)_4NPF_6$, and mixtures thereof and wherein said polymeric matrix material is polyethylene oxide.

12. The electrolyte of claim 11 wherein said plasticizer is polyethylene glycol dimethyl ether.

13. A method of making an environmentally stable solid, ionically conductive, thin film electrolyte system comprising the steps of:

Preparing a solution by combining an amount of symmetrical tetraalkylammonium electrolyte salt and an amount of organic, polymeric complexing matrix material, said matrix material being one containing conducting donor atoms capable of complexing with the cations of the electrolyte salt, in an amount of an aprotic organic solvent and an amount of organic plasticizer forming a mixture thereof;

coating said mixture on a substrate, to form a film thereof;

evaporatively removing said solvent at a temperature in the range from about 30° C. to about 150° C. for a time sufficient to convert the composite consisting essentially of an amount of plasticizer, said electrolyte salt and said complex matrix material to a predominately amorphous form.

14. The method of claim 13 wherein said electrolyte salt is selected from the group consisting of $(CH_3)_4NPF_6$, $(C_2H_5)_4NPF_6$, $(C_3H_7)_4NPF_6$, $(C_4H_9)_4NPF_6$, and mixtures thereof; wherein said polymeric complexing matrix material is selected from the group consisting of polyethylene oxide, polypropylene oxide, polyvinylidene fluoride and polyacrylonitrile; and wherein said aprotic organic solvent is selected from the group consisting of acetonitrile, γ-butyrolactone, propylene carbonate, dimethylformamide, tetrahydroforan and combinations thereof and wherein said organic plasticizer is polyethylene glycol dimethyl ether.

15. The method of claim 14 further comprising the step of spin coating said mixture on a substrate prior to removal of said solvent and said plasticizer.

16. The method of claim 15 wherein said electrolyte salt is selected from $(C_2H_5)_4NPF_6$ and $(C_4H_9)_4NPF_6$ and mixtures thereof, said complexing polymer matrix material is polyethylene oxide, said solvent is propylene carbonate.

17. The method of claim 16 wherein the polyethylene oxide to salt molar ratio is in the range of 5:1 to 15:1 and the amount of polyethylene glycol dimethyl ether is in the range of 5% to 30% by weight.

18. The method of claim 16 wherein the polyethylene oxide salt ratio is in the range of 9:1 to 12:1 and the amount of polyethylene glycol dimethyl ether is approximately 20%.

19. The method of claim 16 wherein said solvent and plasticizer are removed at a temperature from about 40° C. to 150° C.

20. An electrochemical sensor comprising:

a dielectric substrate;

an electrode pattern including working, counter and reference electrodes on said substrate;

an environmentally stable, solid, ionically conductive electrolyte system coated on said electrolyte pattern in composite film form and consisting essentially of an amount of plasticizer, an amount of symmetrical tetraalkylammonium electrolyte salt and an amount of organic polymeric complexing matrix material, said matrix material being one containing donor atoms capable of complexing with the cations of the electrolyte salt wherein said composite is predominately in an amorphous form; and circuit means configured to apply desired potential differences between the working electrode and the reference electrode and including means to measure cell output based on the reduction/oxidation of a species of interest.

21. The electrochemical sensor of claim 20 wherein said symmetrical electrolyte salt is selected from the group consisting of $(CH_3)_4NPF_6$ $(C_2H_5)_4NPF_6$, $(C_3H_7)_4NPF_6$, $(C_4H_9)NPF_6$, and mixtures thereof; and wherein said polymeric matrix material is selected from the group consisting of polyethylene oxide, polyproplyene oxide, polyvinylidene fluoride and polyacrylonitrile.

22. The electrochemical sensor of claim 21 wherein said film electrolyte system has a thickness ≦5 mils.

23. The electrolyte of claim 21 wherein said plasticizer is polyethylene glycol dimethyl ether.

24. The electrochemical sensor of claim 20 wherein said electrolyte salt is selected from $(C_2H_5)_4NPH_6$ and $(C_4H_9)_4NPF_6$ and mixture thereof and said complexing polymer matrix material is polyethylene oxide.

25. The electrochemical sensor of claim 24 wherein said film electrolyte system has a thickness ≦5 mils.

26. The electrolyte of claim 24 wherein said plasticizer is polyethylene glycol dimethyl ether.

* * * * *

UNITED STATES PATENT AND TRADEMARK OFFICE
CERTIFICATE OF CORRECTION

PATENT NO.   : 4,948,490
DATED        : August 14, 1990
INVENTOR(S)  : H. V. Venkatasetty It is certified that error appears in the above-identified patent and that said Letters Patent is hereby corrected as shown below:

SUMMARY OF INVENTION, Column 2, Line 6, cancel "9as" and substitute --gas--

Signed and Sealed this

Seventh Day of January, 1992

Attest:

HARRY F. MANBECK, JR.

*Attesting Officer*     *Commissioner of Patents and Trademarks*